(12) United States Patent
Honda et al.

(10) Patent No.: US 8,294,090 B1
(45) Date of Patent: Oct. 23, 2012

(54) SUBSTRATE FOR MALDI-TOF MS AND MASS SPECTROMETRY METHOD USING THE SAME

(75) Inventors: Aki Honda, Yokohama (JP); Koji Suzuki, Yokohama (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 254 days.

(21) Appl. No.: 11/666,462

(22) PCT Filed: Oct. 28, 2005

(86) PCT No.: PCT/JP2005/019900
§ 371 (c)(1),
(2), (4) Date: Aug. 21, 2007

(87) PCT Pub. No.: WO2006/046697
PCT Pub. Date: May 4, 2006

(30) Foreign Application Priority Data

Oct. 29, 2004 (JP) .................................. 2004-315699

(51) Int. Cl.
*G01N 27/62* (2006.01)
(52) U.S. Cl. ........ 250/288; 250/281; 250/282; 250/287; 435/6
(58) Field of Classification Search .................. 250/288, 250/287, 281, 282; 435/6
See application file for complete search history.

(56) References Cited

U.S. PATENT DOCUMENTS

| | | | |
|---|---|---|---|
| 6,716,629 B2 * | 4/2004 | Hess et al. | 435/420 |
| 6,846,638 B2 * | 1/2005 | Shipwash | 435/7.1 |
| 7,202,472 B2 * | 4/2007 | Schmucker et al. | 250/288 |
| 7,521,672 B2 * | 4/2009 | Sato et al. | 250/288 |
| 2002/0187312 A1 * | 12/2002 | Fonash et al. | 428/195 |
| 2003/0113709 A1 * | 6/2003 | Alivisatos et al. | 435/4 |
| 2004/0038423 A1 * | 2/2004 | Smirnov et al. | 436/173 |
| 2004/0094705 A1 * | 5/2004 | Wood et al. | 250/288 |
| 2004/0104343 A1 * | 6/2004 | Furuta et al. | 250/288 |
| 2004/0209294 A1 | 10/2004 | Machida et al. | |
| 2005/0037516 A1 * | 2/2005 | Schmucker et al. | 436/173 |
| 2005/0181195 A1 * | 8/2005 | Dubrow | 428/297.4 |
| 2007/0218459 A1 * | 9/2007 | Miller et al. | 435/6 |
| 2007/0298515 A1 * | 12/2007 | Diamond et al. | 436/173 |
| 2008/0073505 A1 * | 3/2008 | Niu et al. | 250/288 |
| 2008/0198376 A1 * | 8/2008 | Poponin | 356/301 |

FOREIGN PATENT DOCUMENTS

| | | |
|---|---|---|
| JP | 2003-247983 A | 9/2003 |
| JP | 2004-125785 A | 4/2004 |
| JP | 2004-184137 A | 7/2004 |

OTHER PUBLICATIONS

Nui et al. U.S. Appl. No. 60/611,116, filed Sep. 17, 2004.*
Poponin U.S. Appl. No. 60/572,959, filed May 19, 2004.*

* cited by examiner

*Primary Examiner* — Michael Logie
(74) *Attorney, Agent, or Firm* — Birch, Stewart, Kolasch & Birch, LLP

(57) ABSTRACT

Disclosed is a MALDI-TOF MS plate with which mass spectrometry may be performed with high reproducibility, and mass spectrum may easily be obtained even when the sample is a macromolecular substance such as a protein or nucleic acid, as well as mass spectrometry by MALDI-TOF MS using the plate. The MALDI-TOF MS plate has nanodot regions having a surface formed of a material which easily adsorbs nucleic acids and/or proteins, to which regions a test sample is attached. The mass spectrometry of a nucleic acid or protein is carried out by performing MALDI-TOF MS using this plate and using the nucleic acid or protein as a test sample.

8 Claims, 4 Drawing Sheets

60, 90, 120, 120nm pitch

Pitch of Dots (nm)

SUBSTRATE FOR MALDI-TOF MS AND MASS SPECTROMETRY METHOD USING THE SAME

TECHNICAL FIELD

The present invention relates to a plate for MALDI-TOF MS and to a method for mass spectrometry using the same.

BACKGROUND ART

MALDI-TOF MS (Matrix Assisted Laser Desorption Ionization-Time Of Flight Mass Spectrometry) is a method widely used in mass spectrometry of biological macromolecules and the like. MALDI is a method for ionizing a test sample by mixing the test sample with a matrix (a compound which absorbs laser light) and by irradiating the test sample with a laser beam for a time as short as several nanoseconds. MALDI is characterized in that it ionizes a wide variety of biological substances under mild conditions under which the biological substances are not substantially decomposed. TOF MS is a method for calculating the mass of the sample wherein the sample is accelerated between electrodes across which a high voltage is applied, the accelerated sample is introduced into a tube called flight tube containing high vacuum, electric field-free region to make the sample fly at a uniform velocity, and wherein the time required for flying a prescribed distance is measured. In theory, since even if the mass is large, only the measurement time is prolonged and there is no theoretical measurement limit, it is a mass spectrometry suited for macromolecules.

Conventionally, as the plates for MALDI-TOF MS, aluminum plates having a coating film made of gold or a self-assembled monolayer have been used. However, the mass spectrometry of a protein or DNA using the conventional plate for MALDI-TOF MS has a problem in that the reproducibility is poor and a spectrum is hardly obtained for a test substance having a large molecular weight. This tendency is prominent for DNAs, so that the number of cases where MALDI-TOF MS was effectively used for the analysis of DNA is small.

Patent Literature 1: JP-A-2001-13110
Patent Literature 2: JP-A-2004-266100
Patent Literature 3: U.S. Pat. No. 6,743,607
Patent Literature 4: U.S. Pat. No. 6,693,187
Patent Literature 5: US-A-2003/0220254
Non-patent Literature 1: Koomen, J. et al., Anal. Chem., 72: 3860 (2000)
Non-patent Literature 2: Vorm, O. et al., Anal. Chem., 66: 3287 (1994)
Non-patent Literature 3: Berggren, W. T., et al., Anal. Chem., 74: 1745 (2002)
Non-patent Literature 4: Papac, D. I. et al., Anal. Chem., 68: 3215 (1996)
Non-patent Literature 5: Hung, K. C. et al., Anal. Chem., 70: 3088 (1998)

DISCLOSURE OF THE INVENTION

Problem which the Invention Tries to Solve

An object of the present invention is to provide a plate for MALDI-TOF MS with which mass spectrometry may be carried out with a high reproducibility and with which mass spectrum may easily be obtained even if the sample is a macromolecular substance such as a protein or nucleic acid, and to provide a mass spectrometry by MALDI-TOF MS using the plate.

Means for Solving the Problem

The present inventors intensively studied to discover that mass spectrometry may be carried out with a high reproducibility and with which mass spectrum may easily be obtained even if the sample is a macromolecular substance such as a protein or nucleic acid by forming tiny nanodot region(s) to which a test substance is attached (hereinafter referred to as "test substance-attaching region"), formed of a material which easily adsorbs nucleic acids and/or proteins on a plate for MALDI-TOF MS and by carrying out MALDI-TOF MS attaching the test substance to the above-described nanodot region(s), thereby completing the present invention.

That is, the present invention provides a plate for MALDI-TOF MS, comprising a nanodot region to which a test substance is to be adsorbed, said nanodot region having a surface formed of a material which easily adsorbs nucleic acids and/or proteins. The present invention also provides a method of mass spectrometry comprising carrying out MALDI-TOF MS using the plate according to the present invention and using a nucleic acid(s) and/or protein(s) as a test sample.

Effects of the Invention

By the present invention, a plate for MALDI-TOF MS with which mass spectrometry may be carried out with a high reproducibility and with which mass spectrum may easily be obtained even if the sample is a macromolecular substance such as a protein or nucleic acid, as well as a mass spectrometry by MALDI-TOF MS using the plate, was provided. By using the plate according to the present invention, measurement results may be obtained with high reproducibility, mass spectrum may easily be obtained, and the peaks are clear, so that accurate measurement may be attained, even when the test substance is a protein or nucleic acid. Therefore, it is expected that the present invention will greatly contribute to mass spectrometry of biological substances such as proteins and nucleic acids.

BEST MODE FOR CARRYING OUT THE INVENTION

Figure 1:
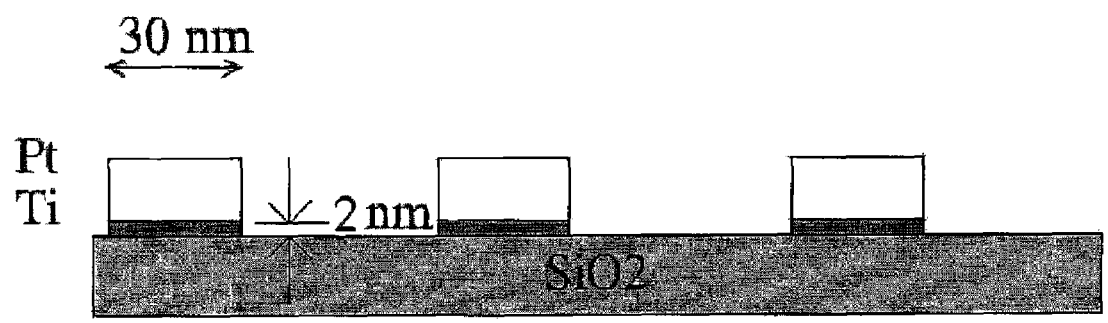
FIG. 1 is a schematic sectional view of a plate for MALDI-TOF MS, having nanodot regions, which was prepared in an example of the present invention.

As described above, the plate for MALDI-TOF MS according to the present invention comprises a nanodot region whose surface is made of a material which easily adsorbs nucleic acids and/or proteins, on which the test substance is to be attached. At least the surface of the nanodot region is formed of a substance (hereinafter referred to as simply "easily-adsorbing substance") which easily adsorbs nucleic acids and/or proteins. Examples of the easily-adsorbing substance include metals other than alkali metals and alkaline earth metals, such as gold, platinum, silver, copper and iron (as well as alloys between them); and hydrophobic polymers such as polystyrene, polyethylene and polypropylene. Among these, gold, platinum and titanium, which are thermally and chemically stable during processing and during measurements are preferred. Although it is required that the surface of the test substance-attaching region be formed of an easily-adsorbing substance, an underlayer thereof may be made of a different substance. For example, an adhesive layer for promoting adhesion of the region with the substrate may be interposed. In the examples below, although platinum or gold is used as the easily-adsorbing substance, the platinum layer or gold layer is formed on the surface of a silicon oxide film via a titanium layer.

In the plate for MALDI-TOF MS according to the present invention, the region(s) to which the test substance is attached (hereinafter also referred to as "test substance-attaching region(s)") is(are) the nanodot region(s) formed of the above-described easily-adsorbing substance. The term "nanodot region" herein means a tiny region having a diameter of less than 1 μm, preferably about 10 nm to 150 nm, more preferably about 20 nm to 40 nm. The shape of the nanodot region is not restricted to circular, but may be in the form of other shape, for example, a polygon such as triangle, square, rectangle, pentagon, hexagon or octagon; or oval. In case of a shape other than circle, if the major axis or the longest side is within the above-described range, the region is included in the "nanodot region" as defined in the present invention. It is preferred, however, that the minor axis or the shortest side is also within the above-described range. In view of the ease of production, circular shape is especially preferred.

In the present invention, it is an important feature that the test substance-attaching region(s) be in the form of nanodot region(s). As described above, MALDI-TOF MS plates whose surface is made of gold are known and commercially available. As described above, gold is an easily-adsorbing substance which may preferably be employed in the present invention. The present inventors surprisingly discovered that by forming the region(s) to which the test substance is to be attached in the form of nanodot region(s), mass spectrometry of macromolecular substances such as proteins and nucleic acids may be carried out with a higher reproducibility and mass spectrum may be more easily obtained than in cases where a MALDI-TOF MS plate made of the same easily-adsorbing substance, which does not have a nanodot region, and reached the present invention based on this discovery. Although the mechanism by which the reproducibility of the mass spectrometry is improved and mass spectrum is easily obtained is not well understood, observation with an electron microscope revealed that the crystalline state of the test substance is different. More particularly, the present inventors confirmed that in cases where the test substance is a linear polymer such as a nucleic acid, needle-shaped crystals are formed on the nanodot region(s), while aggregated crystals are formed on the known plates which do not have a nanodot region, so that the test substance is better dispersed and crystallized more orderly when the plate of the present invention is used.

Although the material of the substrate on which the test substance-attaching region(s) is(are) formed is not restricted, the substrate is preferably made of a material hardly adsorbing nucleic acids and proteins (hereinafter simply referred to as "hardly adsorbing"). That is, in a preferred mode of the present invention, the nanodot region(s) whose surface is made of an easily-adsorbing substance is(are) formed on a hardly adsorbing substrate. Preferred examples of the hardly adsorbing materials include silicon and silicon oxide. Since micromachining techniques of silicon substrates and silicon substrates coated with silicon oxide coating films have been established so that the grooves and the like described below may easily be formed, use of the silicon or silicon oxide substrate is preferred from this point too. By forming the nanodot region(s) with an easily-adsorbing substance and by forming the substrate (i.e., the vicinity(ies) of the nanodot region(s)) with a hardly adsorbing material, the advantageous effects of the present invention, that is, the effects that mass spectrometry of macromolecular substances such as proteins and nucleic acids may be carried out with high reproducibility and mass spectra may easily be obtained, may be further promoted. Although the mechanism thereof is not well understood, it is presumed that the test substance contained in the test sample added to the plate more or less gather on the nanodot region(s) (since the nanodot region(s) is(are) so small that it(they) cannot be seen with a light microscope, the test sample is spotted not on the nanodot region(s) alone, but applied on a relatively large area including the nanodot region(s), the test sample is applied to the regions other than the nanodot region(s)), and this influence on the crystallization of the test substance on the nanodot region(s).

To increase measurement sensitivity, a plurality of nanodot regions are usually formed on one substrate. In cases where a plurality of nanodot regions are formed, although the pitch of the array (the distance between centers of a plurality of nanodot regions) is not restricted, densification may be attained by making the pitch small. Therefore, the pitch is preferably not more than 1000 nm, more preferably not more than 600 nm. Since a plurality of nanodot regions are apart each other, the lower limit of the pitch is inevitably larger than the diameter of the nanodot regions, and is preferably not less than twice the diameter of the nanodot regions. In cases where a plurality of nanodot regions are formed, although it is preferred to form the nanodot regions with the same easily-adsorbing substance in view of ease of production, nanodot regions formed of different easily-adsorbing substances may be used in combination.

A group of nanodot regions may be formed in an area encircled by a groove formed in the substrate, and a plural number of such groups (spots) may be formed. If the nanodot regions are grouped as such, the plate may be used conveniently in experimental procedures, for example, such that the same test sample is measured in each group, and different test samples are measured in different groups. Since the test sample dropped on a spot does not flow outside the groove defining the spot, contamination of test samples between different spots may be prevented. The size of such a spot is not restricted at all, and usually about 0.5 mm to 5 mm in diameter.

The nanodot regions may be formed on a substrate by a known method. For example, in cases where the easily-adsorbing substance is a metal, the nanodot regions may easily be formed by vacuum deposition or the like using a photoresist or an electron resist. As the vacuum deposition, electron beam (EB) deposition which can easily form a uniform film is preferred. A method for preparing the test substance-attaching regions whose surface is made of platinum using EB deposition is concretely described in the examples below.

The mass spectrometry by MALDI-TOF MS according to the present invention may be carried out in exactly the same manner as in the conventional MALDI-TOF MS except that the above-described plate according to the present invention is used and that a mixture of the test sample and a matrix is attached to the above-described test substance-attaching regions, and a concrete example thereof is described in the examples below. In the plate according to the present invention, the test substance-attaching regions are the nanodot regions. However, since the nanodot regions are so small that they cannot be seen with a light microscope, it is difficult to selectively spot the test sample on only the nanodot regions, and the test sample is applied to a larger area including the nanodot regions. Therefore, the test sample is applied to the regions other than the nanodot regions. The amount of the test sample applied to the plate is not restricted, and usually about 0.5 to 5 µL, especially about 1 to 2 µL. The concentration of the test substance (the nucleic acid, protein or the like to be assayed by mass spectrometry) is not restricted, and usually about 0.1 µM to 100 µM, preferably about 1 µM to 50 µM.

The present invention will now be described more concretely by way of Examples thereof. It should be noted, however, that the present invention is not restricted to the Examples below.

EXAMPLE 1

Preparation of Plate Having Platinum Nanodot Regions

On a silicon substrate having a diameter of 2 inches, whose surface was coated with a thermally oxidized layer with a thickness of 1 µm, the nanodot regions schematically shown in FIG. 1 were formed by EB deposition using an electron resist. The titanium underlayer had a thickness of 2 nm and a diameter of 30 nm. The upper platinum layer had a thickness of 50 nm and a diameter of 30 nm. The pitch between the nanodot regions (in both of the vertical and lateral directions) was 60 nm, 90 nm or 120 nm. The nanodot regions were formed in areas (spots) each of which was encircled by a ring-shaped groove having a diameter of 2.4 to 2.5 mm, width of 100 µm and a depth of 190 nm or 250 nm, thereby grouping the nanodot regions.

More concretely, the above-described steps were performed by the following steps: That is, first, as an underlayer resist, an electron positive-working resist ZEP520 (produced by ZEON CORPORATION) was applied by spin-coating (film thickness: 50 nm), and the resultant was prebaked in an oven at 165° C. for 30 minutes. Thereafter, as an upper layer resist, ZEP520 resist (produced by ZEON CORPORATION) supplemented with 20% fullerene (C60/70) was applied by spin-coating (film thickness: 40 nm), and the resultant was prebaked in an oven at 165° C. for 30 minutes. Using an EB writer JBX9300FS (produced by JEOL LTD.) 100 kV, 7nA (beam diameter: about 20 nm), EB was radiated to the regions at which the nanodot regions are to be formed, and the resultant was immersed in a developer ZED-N50 (produced by ZEON CORPORATION) for 60 seconds to carry out developing. Thereafter, by EB deposition using a commercially available EB deposition apparatus, a titanium layer with a thickness of 2 nm was deposited, and a platinum layer with a thickness of 50 nm was deposited on the titanium layer. The resultant was immersed in Shifley Remover 1165 (trademark) to develop the resist, thereby leaving the nanodot regions alone each of which was constituted by the titanium layer and the platinum layer laminated thereon. Then ring-shaped grooves were formed in the silicon oxide film to encircle each of the groups of the nanodot regions formed earlier by each of the ring-shaped grooves. This operation was carried out concretely as follows: An electron beam resist, ZEP resist (produced by ZEON CORPORATION) was applied by spin-coating (film thickness: 250 nm), and the resultant was prebaked in an oven at 165° C. for 30 minutes. With a an EB writer JBX9300FS (produced by JEOL LTD.) 100 kV, 7nA (beam diameter: about 20 nm), EB was radiated to the regions at which the grooves are to be formed. The resultant was immersed in a developer ZED-N50 (produced by ZEON CORPORATION) for 120 seconds to carry out developing. Thereafter, with a reactive ion etching apparatus 10-NR. (produced by Samco), $CHF_3$ gas reactive ion etching (RIB) was performed at an output of 100 W and a gas pressure of 0.8 Pa. The resist was then removed by $UV/O_3$ treatment.

Figure 2:
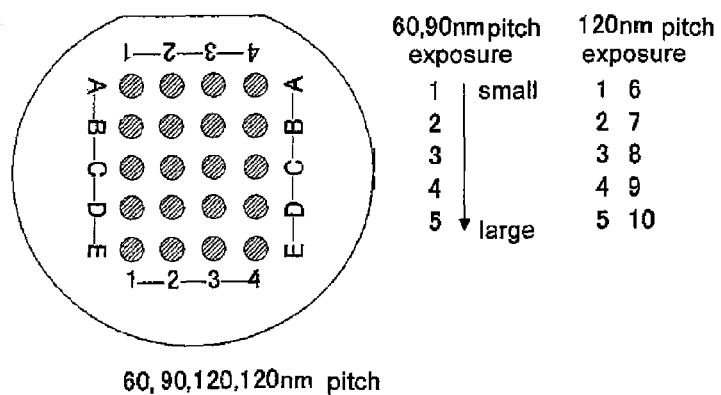
FIG. 2 is a schematic plan view for explaining a method for designating each spot in a plate for MALDI-TOF MS, having nanodot regions, which was prepared in an example of the present invention.

As shown in FIG. 2, the spots each of which was encircled by each ring-shaped groove were identified such that the number 1, 2, 3 or 4 was assigned in the vertical direction (setting the straight portion of the substrate at the left side), and A, B, C, D or E was assigned in the lateral direction (Each spot was identified as, for example, A1, C3 or the like). Since fluctuation in production may occur, plates were prepared varying the exposure during the writing of the nanodots in each spot within the range from 1 to 10.

Observation with a scanning electron microscope revealed that in two spots at which the exposure was too much among the nanodot regions formed with a pitch of 60 nm and 120 nm, respectively, metal was left in the areas other than the nanodot regions, but in the spots other than these spots, the desired nanodot regions alone were left on the substrate, so that the plates of the present invention were obtained.

EXAMPLE 2

MALDI-TOF MS of DNAs

On the nanodot regions of the plate prepared in Example 1, a mixture of test substances and a matrix 3-HPA (3-hydroxypicolinic acid) was spotted, which test substances were the three types of DNAs (having a size of 16-mer ("mer" means the number of bases"), 19-mer and 24-mer, respectively, and a molecular weight of 4893.16, 5815.67 and 6713.28, respectively) having the following sequences, respectively:

```
5'-act tct gtg ttt agg t-3'
5'-act tct gtg ttt agg tgt c-3'
5'-act tct gtg ttt agg tgt ctc tca-3'
```

This operation was carried out concretely as follows: DNAs were dissolved in MilliQ water to a concentration of 5 pmol/μl each to prepare a mixed solution. On the plate, 1 μl of the sample solution and 1 μl of 3-HPA solution were dropped to mix them, and the resulting mixture was dried in the air. The plate was mounted on an adaptor for setting the plate in an apparatus. The resultant was set in a MALDI-TOF MS apparatus (produced by Bruker Daltonics Inc.), and MALDI-TOF MS was carried out as described in the instructions attached to the apparatus to draw a chart of mass spectrum. On the other hand, for comparison, the same sample was spotted on a silicon substrate on which the nanodot regions were not formed and in which the ring-shaped grooves were formed, and on a commercially available plate for MALDI-TOF MS (aluminum plate having a coating film thereon), and MALDI-TOF MS was performed in the same manner. The results are shown in FIG. 3.

Figure 3:
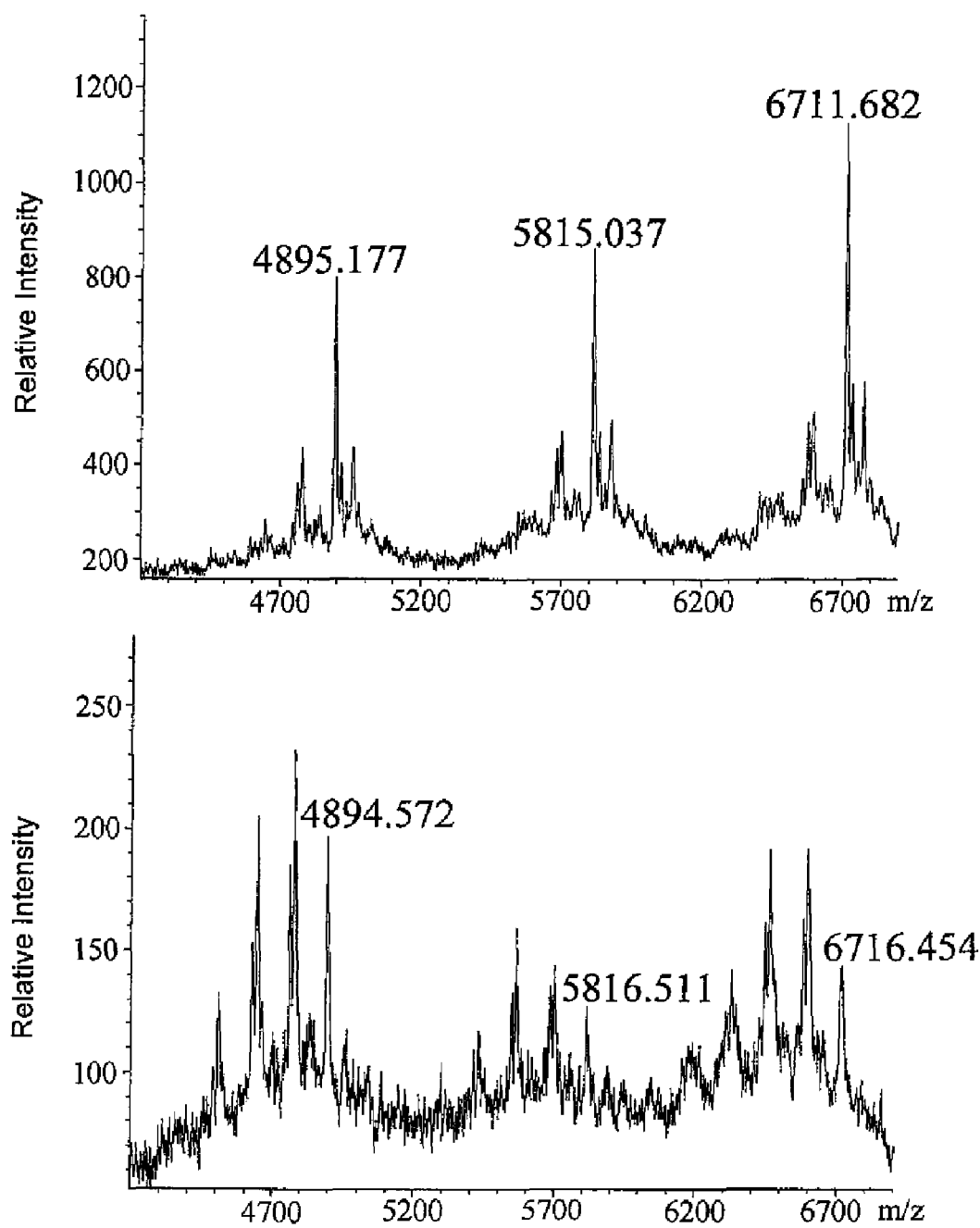
FIG. 3 shows the mass spectra obtained by subjecting a DNA mixture to mass spectrometry by MALDI-TOF MS using the plate of the present invention (upper chart) and using a commercially available plate (lower chart), respectively, which were carried out in an Example of the present invention.

In FIG. 3, the upper chart shows the mass spectrum obtained by using the plate according to the present invention prepared in Example 1, and the lower chart shows the mass spectrum obtained by using the commercially available plate. As can be seen from FIG. 3, when the plate according to the present invention was used, the peaks of each oligonucleotide were clearer and the measured masses were more accurate than those obtained by using the commercially available plate. When the silicon substrate on which the nanodot regions were not formed and in which the ring-shaped grooves were formed was used, no effective spectrum was obtained in any of the spots.

EXAMPLE 3

Reproducibility of MALDI-TOF MS

Figures 4, 5:
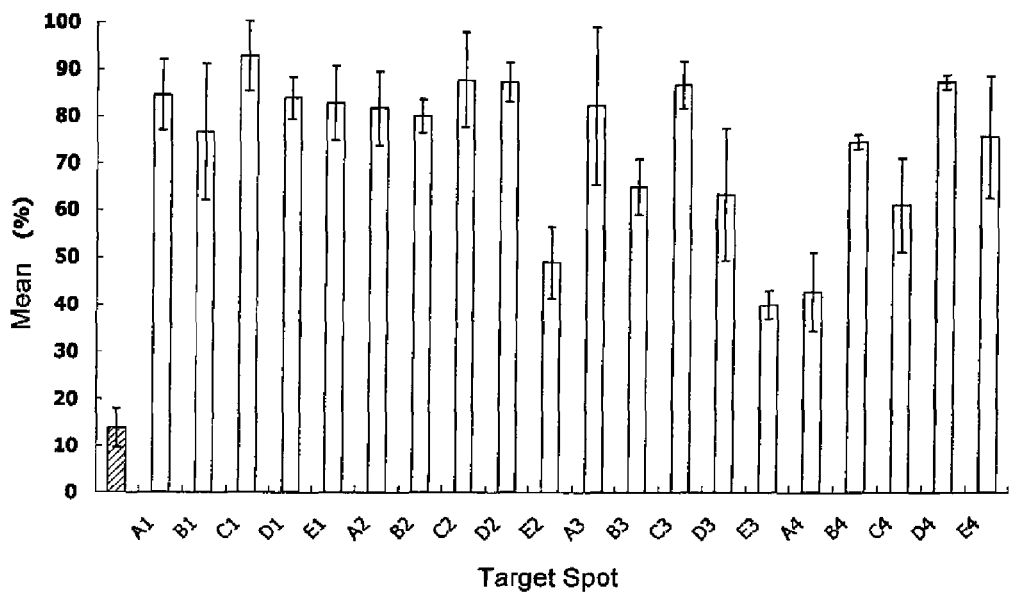
FIG. 4 shows the probabilities that a mass spectrum was obtained by subjecting a DNA mixture to mass spectrometry by MALDI-TOF MS using the plate according to the present invention (Spots A1 to E4) and using a commercially available plate (left end), respectively, which were carried out in an Example of the present invention.
FIG. 5 shows the mass spectra obtained by subjecting a DNA consisting of 40-mer polyC to mass spectrometry using the plate according to the present invention (upper chart) and using a commercially available plate (lower chart), respectively, which were carried out in an Example of the present invention.

Using the same DNA sample as in Example 2, MALDI-TOF MS was carried out in the same manner as in Example 2, and reproducibility was evaluated. Sixty sites were randomly selected from the sample spots, and the probabilities that a mass spectrum was obtained when a laser light was radiated are shown in FIG. 4. Those wherein S/N ratio was not less than 5, dissolution (m/difference m) was not less than 250, and wherein signal intensity of not less than 300 were regarded as signals, and standard deviation was calculated (N=3).

A1 to E1 had a dot pattern of 60 nm pitch, A2 to E2 had a dot pattern of 90 nm pitch, and A3 to E4 had a dot pattern of 120 nm pitch. The different numberings in the same pitch was because of the difference in the dot size due to the difference in exposure during the production step of the nanodot plate. The left most bar along the abscissa shows the result when the commercially available plate was used, and the probability that a spectrum was obtained was only about 15%. The bars along the abscissa other than the left most one show the results of each spot of the plate according to the present invention. With any spot, the probability was much higher than that with the commercially available plate. Thus, it is seen that measurement may be carried out with a high reproducibility by using the plate of the present invention.

EXAMPLE 4

MALDI-TOF MS of Macromolecular DNAs

MALDI-TOF MS was performed on DNAs consisting of polyC of 40-mer and 50-mer (M.W. 11,520 and 14,412), respectively, in the same manner as in Example 2, thereby searching the detection limit of the long chain DNAs. The results are shown in FIG. 5.

The upper chart in FIG. 5 shows the mass spectrum of the 40-mer DNA, which was obtained by using the plate according to the present invention prepared in Example 1, and the lower chart shows the mass spectrum of the 40-mer DNA, which was obtained by using the commercially available plate. As is apparent from FIG. 5, the measurement of the 40-mer DNA using the plate according to the present invention succeeded in increase in the S/N ratio and in the detection sensitivity.

EXAMPLE 5

Linearity of Relationship Between Concentration and Peak Ratio

MALDI-TOF MS was carried out in the same manner as in Example 2 for a 23-mer DNA having a varying concentration, using a 24-mer DNA as an internal standard, and the ratio of peak areas in the obtained mass spectra was plotted. The calibration curve was prepared by plotting the mean of 3 runs. For comparison, the same operations were performed using a commercially available MALDI-TOF MS plate. The results are shown in FIG. 6.

Figure 6:
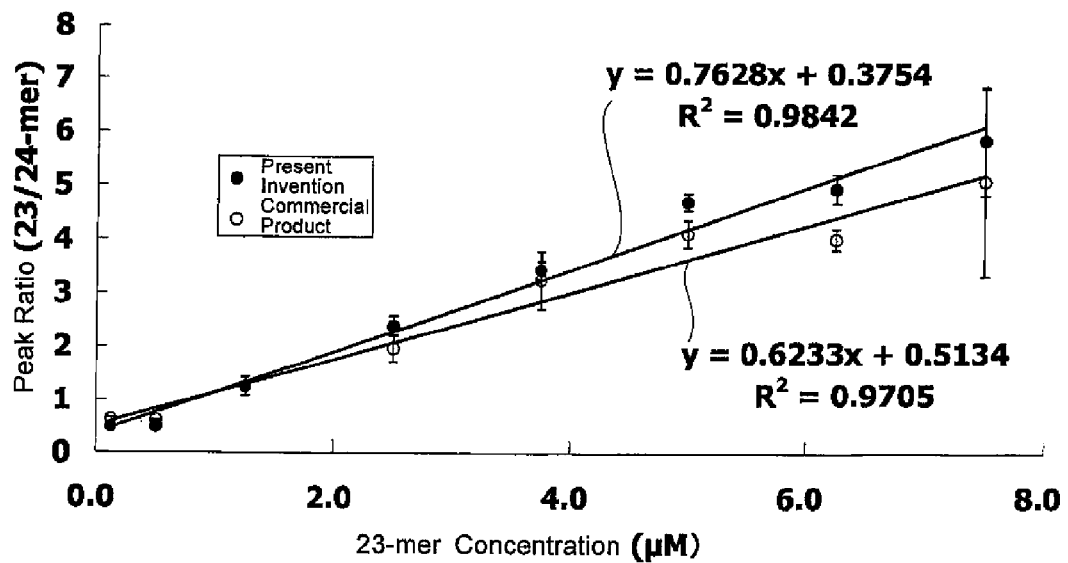
FIG. 6 shows the calibration curves prepared by plotting the ratio of peak areas of the mass spectra obtained by subjecting a 23-mer DNA having varying concentration and a 24-mer DNA as an internal standard to MALDI-TOF MS using the plate of the present invention and a commercially available plate, respectively, which were carried out in an Example of the present invention.

As can be seen from FIG. 6, linearity was observed when the commercially available plate was used, and it was proved that the relationship was not lost even when the plate according to the present invention was used.

EXAMPLE 6

Preparation of Plate Having Gold Nanodot Regions

The same operations as in Example 1 were repeated except that gold was used in place of platinum to obtain a plate having gold nanodot regions. In addition to the nanodot regions having pitches of 60 nm, 90 nm and 120 nm, respectively, nanodot regions having pitches of 240 nm, 480 nm and 1000 nm, respectively, were also formed.

EXAMPLE 7

Preparation of Plate Having Titanium Nanodot Regions

The same operations as in Example 1 were repeated except that the thickness of the titanium layer was 50 nm and that platinum was not deposited on the titanium layer to obtain a plate having titanium nanodot regions. In addition to the nanodot regions having pitches of 60 nm, 90 nm and 120 nm, respectively, nanodot regions having pitches of 240 nm, 480 nm and 1000 nm, respectively, were also formed.

EXAMPLE 8

Preparation of Plate Having Platinum Nanodot Regions (Part 2)

By the same method as in Example 1, a plate having platinum nanodot regions was prepared. In addition to the nanodot regions having pitches of 60 nm, 90 nm and 120 nm, respectively, nanodot regions having pitches of 240 nm, 480 nm and 1000 nm, respectively, were also formed.

EXAMPLE 9

The performance of each of the plates prepared in Examples 6 to 8, in terms of the probability that mass spectrum was obtained (signal-obtaining probability), was measured as in Example 3. The concentration of the DNA was 20 µM, and the matrix solution contained 50 mg/ml of 3-HPA and 5 mg/ml of diammonium citrate in 30% acetonitrile (containing 0.1% TFA).

Figure 7:
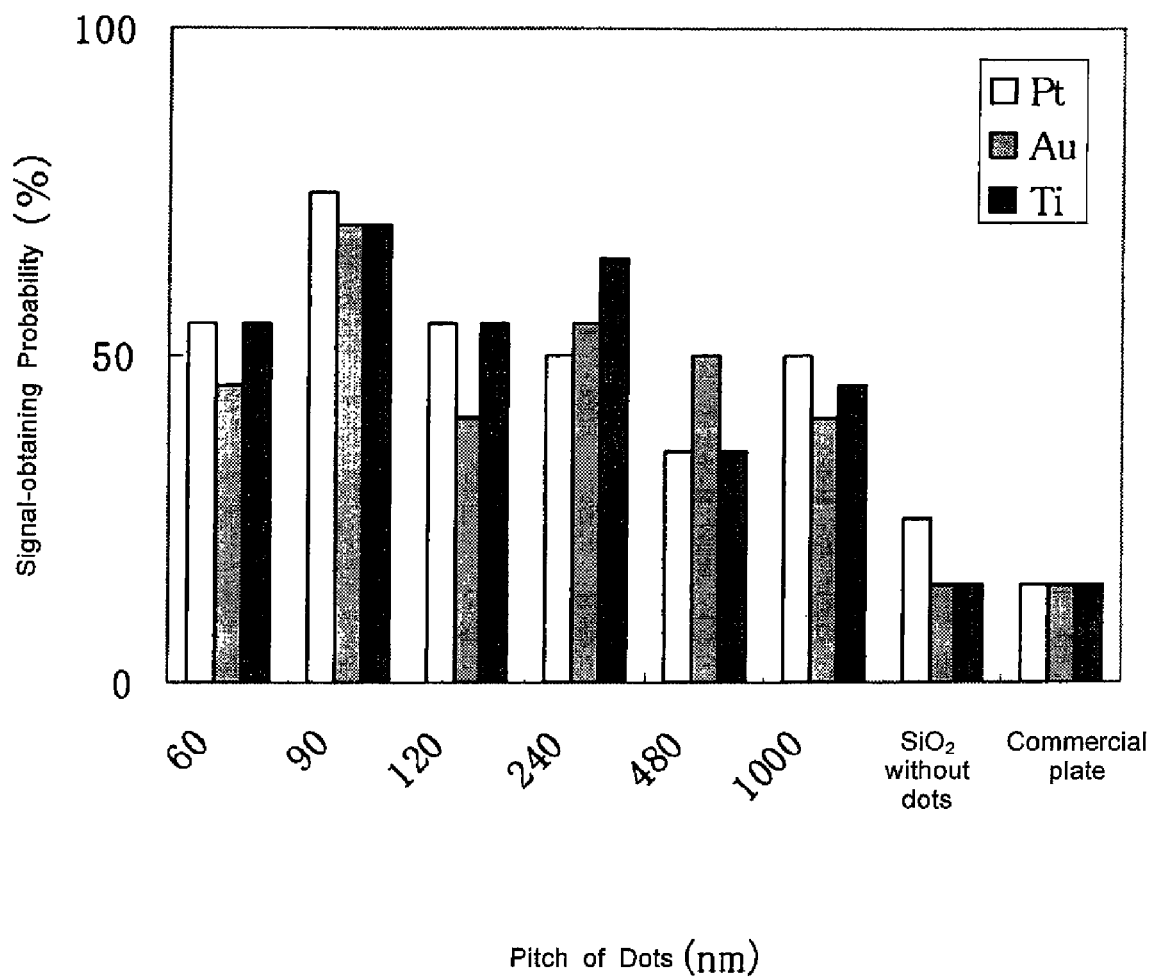
FIG. 7 shows the probabilities (%) that a mass spectrum was obtained by subjecting a DNA mixture to mass spectrometry by MALDI-TOF MS using the plates according to the present invention having nanodot regions formed of platinum, gold and titanium, respectively, and the probabilities obtained when $SiO_2$ substrate having no nanodot regions and a commercially available plate were used, respectively, which were carried out in an example of the present invention.

The results are shown in FIG. 7. As shown in FIG. 7, in any cases where the nanodot regions were formed with platinum, gold or titanium, the signal-obtaining probability was apparently higher than those obtained when the $SiO_2$ substrate having no nanodot regions and the commercially available MALDI-TOF MS plate (coated aluminum plate), respectively, which were comparative controls. As for the pitch of the nanodots, the signal-obtaining probability was higher in any cases where the pitch was within the entire range of 60 nm to 1000 nm, than the comparative controls.

INDUSTRIAL AVAILABILITY

With the MALDI-TOF MS plate according to the present invention, mass spectrometry may be performed with high reproducibility, and mass spectrum may easily be obtained even when the sample is a macromolecular substance such as a protein or nucleic acid. Therefore, by using the plate of the present invention, even if the test substance is a protein or nucleic acid, the measurement results may be obtained with high reproducibility, the mass spectrum may easily be obtained, and the peaks are clear, so that accurate measurement may be attained. Thus, the present invention is useful for the mass spectrometry of biological substances such as proteins and nucleic acids.

---

---

The invention claimed is:

1. A method of mass spectrometry comprising carrying out MALDI-TOF MS using a plate comprising an uncovered and exposed nanodot region to which a test substance is to be adsorbed while the nanodot region is disposed on the plate, said nanodot region having a surface formed of a material which easily adsorbs nucleic acids and/or proteins, and using a nucleic acid(s) and/or protein(s) as a test sample,
wherein said material which easily adsorb nucleic acids and/or proteins is i) a metal other than alkali metals and alkaline earth metals or ii) hydrophobic polymer.

2. The method according to claim 1, wherein said test sample is applied to said nanodot region(s) and to regions other than said nanodot region(s).

3. The method according to claim 1, wherein a plurality of said nanodot regions are formed on said plate.

4. The method according to claim 1, wherein said material which easily adsorb nucleic acids and/or proteins is a metal other than alkali metals and alkaline earth metals.

5. The method according to claim 1, wherein said metal other than alkali metals and alkaline earth metals is platinum, gold or titanium.

6. The method according to claim 1, wherein said metal other than alkali metals and alkaline earth metals is platinum or gold.

7. The method according to claim 1, wherein said nanodot region(s) is(are) formed on a substrate made of a material which hardly adsorbs nucleic acids and/or proteins.

8. The method according to claim 1, wherein at least one surface of said substrate is made of silicon or silicon oxide.

* * * * *

SEQUENCE LISTING

```
<160> NUMBER OF SEQ ID NOS: 3

<210> SEQ ID NO 1
<211> LENGTH: 16
<212> TYPE: DNA
<213> ORGANISM: artificial sequence
<220> FEATURE:
<223> OTHER INFORMATION: oligonucleotide

<400> SEQUENCE: 1
acttctgtgt ttaggt                                                   16

<210> SEQ ID NO 2
<211> LENGTH: 19
<212> TYPE: DNA
<213> ORGANISM: artificial sequence
<220> FEATURE:
<223> OTHER INFORMATION: oligonucleotide

<400> SEQUENCE: 2
acttctgtgt ttaggtgtc                                                19

<210> SEQ ID NO 3
<211> LENGTH: 24
<212> TYPE: DNA
<213> ORGANISM: artificial sequence
<220> FEATURE:
<223> OTHER INFORMATION: oligonucleotide

<400> SEQUENCE: 3
acttctgtgt ttaggtgtct ctca                                          24
```